United States Patent
Pridmore et al.

(10) Patent No.: US 9,309,492 B2
(45) Date of Patent: Apr. 12, 2016

(54) **DERIVATIVE OF THE *LACTOBACILLUS JOHNSONII* STRAIN CNCM I-1225, DEFICIENT IN D-LACTIC ACID PRODUCTION AND WITH AN IMPROVED SHELF LIFE**

(75) Inventors: Raymond-David Pridmore, St-Sulpice (CH); Francis Foata, Lausanne (CH); Michele Delley, Vauderens (CH); Ivana Jankovic, Epalinges (CH)

(73) Assignee: Nestec S.A., Vevey (CH)

( * ) Notice: Subject to any disclaimer, the term of this patent is extended or adjusted under 35 U.S.C. 154(b) by 137 days.

(21) Appl. No.: 14/008,831

(22) PCT Filed: Mar. 29, 2012

(86) PCT No.: PCT/EP2012/055673
§ 371 (c)(1),
(2), (4) Date: Sep. 30, 2013

(87) PCT Pub. No.: WO2012/130966
PCT Pub. Date: Oct. 4, 2012

(65) Prior Publication Data
US 2014/0186317 A1 Jul. 3, 2014

(30) Foreign Application Priority Data
Mar. 29, 2011 (EP) .................................... 11160140

(51) Int. Cl.
| | |
|---|---|
| *A23L 1/30* | (2006.01) |
| *C12N 1/20* | (2006.01) |
| *A23C 9/123* | (2006.01) |
| *C12N 1/04* | (2006.01) |
| *C12N 9/04* | (2006.01) |
| *C12P 7/56* | (2006.01) |
| *C12R 1/225* | (2006.01) |
| *A23L 2/52* | (2006.01) |
| *A61Q 19/00* | (2006.01) |
| *A61K 8/99* | (2006.01) |
| *A61K 35/747* | (2015.01) |

(52) U.S. Cl.
CPC ................ *C12N 1/20* (2013.01); *A23C 9/1234* (2013.01); *A23L 1/3014* (2013.01); *A23L 2/52* (2013.01); *A61K 8/99* (2013.01); *A61Q 19/00* (2013.01); *C12N 1/04* (2013.01); *C12N 9/0006* (2013.01); *C12P 7/56* (2013.01); *C12R 1/225* (2013.01); *C12Y 101/02004* (2013.01); *A23C 2220/202* (2013.01); *A23V 2002/00* (2013.01); *A23Y 2220/43* (2013.01); *A61K 35/747* (2013.01); *A61K 2800/10* (2013.01); *Y02P 20/52* (2015.11)

(58) Field of Classification Search
None
See application file for complete search history.

(56) References Cited

U.S. PATENT DOCUMENTS
6,258,587 B1   7/2001  Delley et al.

FOREIGN PATENT DOCUMENTS
| JP | 7194372 | 8/1995 |
|---|---|---|
| WO | 2004039964 | 5/2005 |

OTHER PUBLICATIONS

Demirci et al., "Enhanced production of D-lactic acid by mutants of *Lactobacillus delbrueckii* ATCC 9649*," Journal for Industrial Microbiology, 1992, vol. 11, pp. 23-28. XP009148925.

Li et al., "Cloning and expression of D-lactate dehydrogenase gene in *Lactobacillus* sp. MD-1," Biosis, Aug. 1, 2004, 5 Pages. XP002639198.

Lapierre et al., "D-lactate dehydrogenase gene (IdhD) inactivation and resulting metabolic effects in the *Lactobacillus johnsonii* strains La1 and N312," Applied and Environmental Microbiology, 1999, vol. 65, pp. 4002-4007. XP002639197.

Chinese Office Action for Patent Application No. P2014-501629 dated Dec. 1, 2015—10 pages.

*Primary Examiner* — Robert Yamasaki
(74) *Attorney, Agent, or Firm* — K&L Gates LLP

(57) ABSTRACT

The present invention generally relates to the field of probiotic bacteria. In particular, the present invention relates to natural derivatives of the *Lactobacillus johnsonii* strain CNCM I-1225 with improved properties. For example, the present invention relates to a natural derivative of the *Lactobacillus johnsonii* strain CNCM I-1225 that is deficient in D-lactic acid production and exhibits an improved viability during product storage.

8 Claims, 4 Drawing Sheets

SEQ ID NO: 6

```
   1  ATGACAAAGA TTTTTGCTTA CGCTATTCGT AAAGATGAAG AACCTTTCTT
  51  AAACGAATGG AAAGATGCAC ACAAGGATAT TGAAGTTGAA TACACTGACA
 101  AGCTTTTAGC CCCTGAAACT GCTAAATTAG CTAAGGGTGC TGACGGTGTT
 151  GTTGTTTACC AACAATTAGA CTACACTCCT GAAACTCTTC AAGCTTTAGC
 201  TGATGCTGGC GTAACTAAGA TGTCATTAC̲A̲ TAACGTTGGT GTTGACAACA
 251  TCGACATGGA CAAGGCTAAA GAATTAGGCT TTGAAATCAC TAACGTTCCT
 301  GTATACTCTC CTGACGCAAT TGCTGAACAT GCTGCAATTC AAGCTGCTCG
 351  CGTACTACGT CAAGATAAGC GTATGGATGA AAAGATGGCT AAGCGCGACT
 401  TACGCTGGGC ACCTACTATT GGTCGTGAAG TTCGTGACCA AGTTGTTGGT
 451  GTTGTAGGTA CTGGTCACAT CGGTCAAGTA TTTATGAAGA TTATGGAAGG
 501  CTTTGGCGCA AAAGTTATTG CTTACGATAT CTTCAAGAAC CCAGAACTTG
 551  AAAAGAAGGG TTACTACGTT GACTCACTTG ATGACTTATA CAAGCAAGCT
 601  GATGTAATTT CACTTCACGT TCCAGATGTT CCAGCAAACG TTCACATGAT
 651  TAATGATGAA TCAATCGCTA AGATGAAAGA TGGCGTTGTA ATCGTAAACT
 701  GCTCACGTGG TCCACTTGTT GACACTGACG CTGTTATCCG CGGCTTAGAT
 751  TCTGGTAAGA TCTTTGGTTT CGTAATGGAC ACTTACGAAG GTGAAGTTGG
 801  TGTATTTAAC GAAGATTGGG AAGGTAAAGA ATTCCCAGAT GCTCGTTTAG
 851  CTGACTTAAT CGATCGTCCA AATGTATTGG TAACTCCACA TACTGCTTTC
 901  TACACTACTC ATGCTGTACG TAACATGGTA ACTAAAGCAT TTGACAACAA
 951  CTTAAAGATG ATCAACGGTG AAAAACCAGA TTCTCCAGTT GCTTTGGACA
1001  AGAACAAGTT CTAA
```

FIGURE 4B

SEQ ID NO: 7

```
  1  MTKIFAYAIR KDEEPFLNEW KDAHKDIEVE YTDKLLAPET AKLAKGADGV
 51  VVYQQLDYTP ETLQALADAG VTKMSL̲H̲NVG VDNIDMDKAK ELGFEITNVP
101  VYSPDAIAEH AAIQAARVLR QDKRMDEKMA KRDLRWAPTI GREVRDQVVG
151  VVGTGHIGQV FMKIMEGFGA KVIAYDIFKN PELEKKGYYV DSLDDLYKQA
201  DVISLHVPDV PANVHMINDE SIAKMKDGVV IVNCSRGPLV DTDAVIRGLD
251  SGKIFGFVMD TYEGEVGVFN EDWEGKEFPD ARLADLIDRP NVLVTPHTAF
301  YTTHAVRNMV TKAFDNNLKM INGEKPDSPV ALDKNKF
```

DERIVATIVE OF THE *LACTOBACILLUS JOHNSONII* STRAIN CNCM I-1225, DEFICIENT IN D-LACTIC ACID PRODUCTION AND WITH AN IMPROVED SHELF LIFE

CROSS REFERENCE TO RELATED APPLICATIONS

The present application is a National Stage of International Application No. PCT/EP2012/055673, filed on Mar. 29, 2012, which claims priority to European Patent Application No. 11160140.7, filed Mar. 29, 2011, the entire contents of which are being incorporated herein by reference.

The present invention generally relates to the field of probiotic bacteria. In particular, the present invention relates to natural derivatives of the *Lactobacillus johnsonii* strain CNCM I-1225 with improved properties. For example, the present invention relates to a natural derivative of the *Lactobacillus johnsonii* strain CNCM I-1225 that is deficient in D-lactic acid production and exhibits an improved viability under oxygen exposure.

*Lactobacillus johnsonii* CNCM I-1225, also known as *Lactobacillus johnsonii* NCC533, or as *Lactobacillus acidophilus* La1, or as *Lactobacillus johnsonii* Lj1, a human isolate (Bernet-Camard, M. F., et al., (1997) Appl. Environ. Microbiol. 63, 2747-2753), is a probiotic that is currently commercialized very successfully under the trademark Lc1.

As it is typical for products containing viable probiotic bacteria, it is a challenge in the production of such products to ensure that the bacteria will remain viable during the shelf life as these micro-organisms are sensitive to oxygen exposure. It would hence be desirable to have available a derivative of *Lactobacillus johnsonii* CNCM I-1225 that exhibits an improved oxygen resistance.

*Lactobacillus johnsonii* CNCM I-1225 has several well documented health benefits, among them, for example activities for immunomodulation (Haller, D., et al., 2000, Infect. Immun. 68:752-759; Haller, D., et al., 2000, Gut 47:79-87; or Ibnou-Zekri, N., et al., 2003, Infect. Immun. 71:428-436), or pathogen inhibition (Bernet, M. F., et al., 1994, Gut, 35:483-489), and a long history of safe use.

One aspect that has limited the application of *Lactobacillus johnsonii* CNCM I-1225 in some product categories, e.g., in products intended for young children and infants, is the production of predominantly the D-lactic acid isomer from the fermentation of sugars. *Lactobacillus johnsonii* CNCM I-1225, for example, if grown in MRS medium, ferments lactose to D- and L-lactic acid in a 60:40% ratio.

The CODEX Infant Formula Directive recommends against the consumption of D-lactic acid and D-lactic acid producing bacteria by infants of less than three years of age due to their limited D-lactic acid elimination that may result in D-lactate acidosis.

The evidence to support this conclusion is limited and based mainly on the presence of D-lactic acid in foods and not on the administration of D-lactic acid producing bacteria, which are natural inhabitants of the gastro-intestinal tract.

Consequently, several publications have challenged this position (Connolly, E. et al., NTRAfoods 3(3), 37-49. 2004; Haschke-Becher, E., et al., 2008, Ann. Nutr. Metab. 53:240-244, Mack, D. R., 2004, Can. J. Gastroenterol. 18:671-675) but so far the recommendation of the CODEX Infant Formula Directive remains unchanged.

The CODEX has essentially excluded D-lactic acid producing probiotics as supplements in infant formulae but has inspired the genetic engineering of strains that produce only L-lactic acid. An example of such a development is the generation of a genetically modified organism (GMO), in particular a genetically modified *Lactobacillus johnsonii* strain, where the d-lactate dehydrogenase (D-LDH) gene (IdhD) was isolated, and an in vitro-truncated cloned copy of the IdhD gene was used to inactivate the genomic copy by gene replacement (Lapierre, L., et al., 1999, Appl. Environ. Microbiol. 65:4002-4007).

This genetically engineered strain was only produced for laboratory purposes and has never been used in food products since its genetic material has been altered using recombinant DNA technologies and the strain is consequently considered a GMO.

Nevertheless, it would be desirable to have available a possibility that allows to make the numerous health benefits of *Lactobacillus johnsonii* strain CNCM I-1225 also available for individuals, for which the consumption of D-lactic acid or of D-lactic acid producing bacteria is currently not advised.

Hence, there is a strong need in the art for a natural probiotic strain, in particular a natural derivative of the *Lactobacillus johnsonii* strain CNCM I-1225, which is deficient in D-lactic acid production and nevertheless viable, and which exhibits an improved survival in the products.

The present inventors have addressed these needs.

Consequently, it was the objective of the present invention to provide the art with a derivative of the *Lactobacillus johnsonii* strain CNCM I-1225, which can also be applied to products intended for infants and young children while respecting the current regulations of the CODEX Infant Formula Directive, which exhibits an improved shelf stability, and which is natural and not considered a GMO.

The present inventors were surprised to see that they could achieve the objective of the present invention by the subject matter of the independent claims. The dependant claims further develop the idea of the present invention.

The inventors have investigated the possibility to isolate a natural (non-GMO), viable and genetically stable variant of *Lactobacillus johnsonii* La1 that produces only L-lactic acid and that has improved storage stability.

Changes in the genome sequence occur naturally, e.g., due to mis-repair of damaged DNA or errors in DNA replication, with a relatively low frequency.

To search for such natural derivatives of the *Lactobacillus johnsonii* strain CNCM I-1225 the present inventors have screened approximately 21,000 colonies of *Lactobacillus johnsonii* CNCM I-1225 and have identified one natural D-lactic acid deficient variant that achieves the object of the present invention.

The present inventors have further determined D- and L-lactic acid concentrations in MRS culture supernatant and have shown that the relative D-lactic acid concentration compared to the total lactic acid concentration in the culture supernatant is below 1.5%; namely about 1.1%.

A DNA sequence analysis identified predominantly point mutations in the lactate dehydrogenase gene that alter the amino acid sequence of the enzyme and hence its catalytic properties.

The natural derivative was shown to be viable and stable with no examples of reversion to D-lactic acid production.

The inventors have also assessed shelf stability at 8° C. and at 15° C. and have compared the identified derivative against *Lactobacillus johnsonii* strain CNCM I-1225. The identified derivative exhibited a significantly improved shelf life compared to *Lactobacillus johnsonii* strain CNCM I-1225. The inventors have also compared the shelf stability of this strain to other derivatives of *Lactobacillus johnsonii* strain CNCM I-1225 and have found that this natural derivative exhibited the best shelf life.

Consequently, one embodiment of the present invention is a natural derivative of the *Lactobacillus johnsonii* strain CNCM I-1225, wherein the derivative of the *Lactobacillus johnsonii* strain CNCM I-1225 is deficient in D-lactic acid production and exhibits an increased shelf life compared to *Lactobacillus johnsonii* strain CNCM I-1225.

To the best knowledge of the inventors this is the first time a natural derivative of the *Lactobacillus johnsonii* strain CNCM I-1225 is provided that is deficient in D-lactic acid production and exhibits an increased shelf life compared to *Lactobacillus johnsonii* strain CNCM I-1225.

"Deficient in D-lactic acid production" means for the purpose of the present invention that a strain produces less than 5%, preferably less than 2%, even more preferred less than 1.5%, and ideally about 1.1% of D-lactic acid compared to the total lactic acid production. The D- and L-lactic acid concentrations can be measured in the cell-free culture supernatant.

The total quantity of lactic acid produced by the natural derivatives of the *Lactobacillus johnsonii* strain CNCM I-1225 is initially related to cell growth. When cells enter into the stationary phase and stop dividing, they continue to metabolise sugar and produce more lactic acid. The ratio of D- and L-lactic acid produced was, however, found to be constant.

A "natural" derivative of the *Lactobacillus johnsonii* strain CNCM I-1225 means a strain which is not considered a GMO. Such a natural derivative may for example be obtained by screening colonies with are subject to changes in the genome sequence that occur naturally, e.g., due to mis-repair of damaged DNA or errors in DNA replication. This natural occurrence of errors may be enhanced by subjecting the colonies to stress conditions, for example by the application of ethyl methane sulfonate, EMS.

For the purpose of this application the term "GMO" shall be defined according to the DIRECTIVE 2001/18/EC OF THE EUROPEAN PARLIAMENT AND OF THE COUNCIL of 12 Mar. 2001 on the deliberate release into the environment of genetically modified organisms and repealing Council Directive 90/220/EEC. Accordingly, a 'genetically modified organism (GMO)' means an organism, with the exception of human beings, in which the genetic material has been altered in a way that does not occur naturally by mating and/or natural recombination.

Within the terms of this definition genetic modification occurs at least through the use of the (1) recombinant nucleic acid techniques involving the formation of new combinations of genetic material by the insertion of nucleic acid molecules produced by whatever means outside an organism, into any virus, bacterial plasmid or other vector system and their incorporation into a host organism in which they do not naturally occur but in which they are capable of continued propagation;

(2) techniques involving the direct introduction into an organism of heritable material prepared outside the organism including micro-injection, macroinjection and micro-encapsulation; or (3) cell fusion (including protoplast fusion) or hybridisation techniques where live cells with new combinations of heritable genetic material are formed through the fusion of two or more cells by means of methods that do not occur naturally.

A strain is considered a "derivative" of the *Lactobacillus johnsonii* strain CNCM I-1225, if it has a nucleic acid identity of at least 99.95%, for example of at least 99.99%, preferably of at least 99.995%. For example, a strain is considered a derivative of the *Lactobacillus johnsonii* strain CNCM I-1225 if it has no more than 500, for example no more than 100, preferably no more than 50 nucleic acid changes compared to the nucleic acid sequence of *Lactobacillus johnsonii* CNCM I-1225.

A bacterial strain is considered as "exhibiting an increased shelf life compared to *Lactobacillus johnsonii* strain CNCM I-1225" if it shows an increased survival in the Lc1 Drink product after 45 days of storage at either 8° C. and/or 15° C. Using the natural derivatives of the *Lactobacillus johnsonii* strain CNCM I-1225 of the present invention in a product will consequently will consequently lead to an increased number of viable bacteria at the end of shelf life.

The present inventors have found that the natural derivatives of the *Lactobacillus johnsonii* strain CNCM I-1225 of the present invention exhibited mutations in the d-ldh gene responsible for the D-lactic acid deficient phenotype.

Consequently, the natural derivatives of the *Lactobacillus johnsonii* strain CNCM I-1225 may have an altered the D-lactate dehydrogenase enzyme sequence. For example, the natural derivative of the *Lactobacillus johnsonii* strain CNCM I-1225 may comprise an arginine to histidine amino acid change at amino acid position 77 of the D-lactate dehydrogenase enzyme sequence.

This change apparently alters D-lactate dehydrogenase enzyme function significantly, so that extremely little or no D-lactic acid is produced.

This change in the D-lactate dehydrogenase enzyme protein sequence is based on a change in the nucleic acid sequence of the D-lactate dehydrogenase gene.

Any natural changes in the nucleic acid sequence of the D-lactate dehydrogenase gene that inactivate the resulting enzyme may achieve the subject matter of the present invention. Also at least one deletion of one or more subsequent nucleotides within the wild-type sequence, or part or the whole of the D-lactate dehydrogenase gene may achieve the subject matter of the present invention.

The present inventors have analyzed the nucleic acid sequence of the D-lactate dehydrogenase gene in the natural derivative of *Lactobacillus johnsonii* CNCM I-1225 of the present invention.

Hence, the present invention also relates to a natural derivative of the *Lactobacillus johnsonii* strain CNCM I-1225, wherein the nucleic acid sequence of the D-lactate dehydrogenase gene in the natural derivative of the *Lactobacillus johnsonii* strain CNCM I-1225 comprises a G to A transition at nucleic acid position 270.

While such a change that results in the inactivation of D-lactate dehydrogenase may occur spontaneously at low frequencies in nature, it is random, and can be repaired back to the parent sequence (wild type) at the same frequency.

This repair frequency may even be higher if the inactivated gene imparts a growth disadvantage to the variant. Given the large number of generations from the culture collection to the final product, it is important that such a change is stable, especially as it is single base-pair change which is genetically less stable than a deletion.

Advantageously, the change also was found to be stable.

One example of a natural derivative of the *Lactobacillus johnsonii* strain CNCM I-1225 that achieves the object of the present invention was isolated, purified and characterized in detail.

The present invention, hence, relates to a natural derivative of the *Lactobacillus johnsonii* strain CNCM I-1225, wherein the natural derivative of the *Lactobacillus johnsonii* strain CNCM I-1225 may be *Lactobacillus johnsonii* CNCM I-4437.

*Lactobacillus johnsonii* CNCM I-4437 was deposited on Feb. 8, 2011, with is the Collection Nationale de Cultures de Microorganismes (CNCM), Institut Pasteur, 25 Rue du Docteur Roux, F-75724 Paris Cedex 15, France, under the Budapest Treaty.

The strain was fully sequenced.

*Lactobacillus johnsonii* CNCM I-1225 was deposited on 30 Jun. 1992, with the CNCM, under the Budapest Treaty.

*Lactobacillus johnsonii* CNCM I-4437 contains a total of 23 changes, including the expected change in the D-lactate dehydrogenase gene responsible for the deficiency in the production of D-lactic acid by this strain. There are changes in two genes whose function is predicted to be important for growth, namely LJ0874—triosephosphate isomerise and LJ0515—phosphomethylpyrimidine kinase. In MRS medium *Lactobacillus johnsonii* CNCM I-4437 grows at a similar rate compared to La1, hence the above changes show no adverse effects. Of note is the secondary change in LJ1658—a histidine kinase enzyme of a two component regulator. Preliminary expression profiling of this strain reveals the significant down-regulation of five genes, LJ1652 to LJ1656, constituting a PTS operon that is possibly specific for mannose. This does not lead to any changes in sugar fermentation patterns compared to La1 but this may be due to the presence of several predicted mannose PTS systems in La1.

The present invention also extends to the natural derivatives of the *Lactobacillus johnsonii* strain CNCM I-1225 in accordance with the present invention, wherein the natural derivative of the *Lactobacillus johnsonii* strain CNCM I-1225 is present as biologically pure culture.

The natural derivatives of the *Lactobacillus johnsonii* strain CNCM I-1225 in accordance with the present invention may be cultured according to any suitable method and may be prepared for addition to the compositions of the present invention by freeze-drying or spray-drying for example.

The probiotic strain *Lactobacillus johnsonii* CNCM I-1225 provides numerous well documented health benefits some of which are detailed above.

"Probiotic" means microbial cell preparations or components of microbial cells with a beneficial effect on the health or well-being of the host. (Salminen 5, et al. "Probiotics: how should they be defined" Trends Food Sci. Technol. 1999:10 107-10).

The natural derivatives of the *Lactobacillus johnsonii* strain CNCM I-1225 in accordance with the present invention may be regarded essentially as bioequivalent in view of the provided health benefits.

Scientific work has shown that also the cell-free culture supernatant isolated from a biologically pure culture of the *Lactobacillus johnsonii* strain CNCM I-1225 has several health benefits (see e.g., Bernet-Camard, M.-F., et al., 1997, APPLIED AND ENVIRONMENTAL MICROBIOLOGY, p. 2747-2753).

Hence, the present invention further extends to the cell-free culture supernatant isolated from a biologically pure culture of a natural derivative of the *Lactobacillus johnsonii* strain CNCM I-1225 in accordance with the present invention.

As the natural derivative of the *Lactobacillus johnsonii* strain CNCM I-1225 and the cell-free culture supernatant of the present invention have numerous health benefits they may be used to treat or prevent disorders in the human or animal body.

Consequently, the present invention relates to a composition comprising the natural derivative of the *Lactobacillus johnsonii* strain CNCM I-1225 and/or the cell-free culture supernatant in accordance with the present invention for use in the preparation of a composition for use in a method for treatment of the human or animal body by therapy.

The present invention also relates to the use of a composition comprising the natural derivative of the *Lactobacillus johnsonii* strain CNCM I-1225 and/or the cell-free culture supernatant in accordance with the present invention in the preparation of a pharmaceutical composition or a medicament.

*Lactobacillus johnsonii* CNCM I-1225 has been extensively studied for its probiotic-associated activities, including immunomodulation (Haller, D., et al., 2000, Infect. Immun. 68, 752-759; Haller, D., et al., 2000, Gut 47, 79-87; Ibnou-Zekri, N., et al., 2003, Infect. Immun. 71, 428-436), pathogen inhibition (Bernet, M. F., et al., 1994, Gut 35, 483-489), and epithelial cell attachment (Neeser, J. R., et al., 2000, Glycobiology 10, 1193-1199; Granato, D., et al., 1999, Appl. Environ. Microbiol. 65, 1071-1077).

Due to bioequivalence, the natural derivatives of the *Lactobacillus johnsonii* strain CNCM I-1225 and/or the cell-free culture supernatant thereof in accordance with the present invention provide the same health benefits.

Consequently, the present invention relates to a composition comprising the natural derivative of the *Lactobacillus johnsonii* strain CNCM I-1225 and/or the cell-free culture supernatant in accordance with the present invention for use in the treatment or prevention of disorders linked to a weakened immune system.

The present invention also relates to the use of the natural derivative of the *Lactobacillus johnsonii* strain CNCM I-1225 and/or the cell-free culture supernatant in accordance with the present invention for the preparation of a composition to treat or prevent disorders linked to a weakened immune system.

Disorders linked to a weakened immune system are well-known in the art and people skilled in the art will understand which disorders are linked to a weakened immune system.

Typical examples of disorders linked to a weakened immune system may be selected from the group consisting of flu, rhinitis, common cold, and combinations thereof.

The composition comprising the natural derivative of the *Lactobacillus johnsonii* strain CNCM I-1225 and/or the cell-free culture supernatant in accordance with the present invention may also be for use in the treatment or prevention of disorders linked to the cell attachment and cell invasion by enterovirulent bacteria or viruses.

The present invention also extends to the use of the natural derivative of the *Lactobacillus johnsonii* strain CNCM I-1225 and/or the cell-free culture supernatant in accordance with the present invention for the preparation of a composition to treat or prevent disorders linked to the cell attachment and cell invasion by enterovirulent bacteria or viruses.

Enterovirulent bacteria and viruses are well known in the art. The European Food Safety Authority (EFSA) has published such a list of pathogens in November 2010.

The enterovirulent bacterial or viral species may for example be selected from the group consisting of *Salmonella*; *Campylobacter*; *Listeria*; *Escherichia coli* strains, such as ETEC, EHEC, EPEC, or EIEC strains, for example; *Yersinia*; *Shigella*; Toxin producing bacteria, such as *Staphylococcus aureus*, *Clostridium botulinum*, or *Bacillus cereus*; *Vibrio vulnificus/parahaemolyticus*; rotavirus; norovirus; verotoxigenic *E. coli*; *Enterobacter sakazakii*; toxigenic *C. perfringens* (type A and B); food-borne parasites, such as *Echino-*

*coccus, Toxoplasma,* or *Giardia; Helicobacter pylori; Clostridium difficile; Clostridium tetani*; or combinations thereof.

It is clear to those skilled in the art, which disorders are linked to what enterovirulent bacterial or viral species.

For example, the disorder linked to the cell attachment and cell invasion by enterovirulent bacterial or viral species may be selected from the group consisting of lower respiratory tract infections, gastro-intestinal tract infections, otitis media, and combinations thereof.

The composition of the present invention may be any kind of composition as long as it is suitable for administration to humans or animals.

The composition of the present invention may in particular be to be administered orally, enterally, parenterally or topically. The compositions may be provided in any galenical form normally available for the selected mode of administration.

The composition of the present invention may be administered to any age group.

Preferably, the composition of the present invention is to be administered during the cold season, e.g., from autumn to spring.

It may also be consumed at any time. It may be preferred to consume the composition of the present invention in the morning, e.g., to boost the immune system for the day.

The composition may, e.g., be selected from the group consisting of food compositions, petfood compositions, drinks, dairy products, nutritional formulas, infant formulas, food additives, nutraceuticals, pharmaceutical compositions, food ingredients and/or cosmetic compositions.

For example, the composition may be selected from the group consisting of acidified milk products, such as yoghurts or yoghurt drinks; or milk based powders.

It may be preferred, in particular for powdered products, if the composition is provided in the form of a shelf stable powder. To obtain shelf stability and to ensure viability of the probiotics the composition may be provided with a water activity smaller than 0.2, for example in the range of 0.19-0.05, preferably smaller than 0.15. Water activity or $a_w$ is a measurement of the energy status of the water in a system. It is defined as the vapor pressure of water deriving from the powder/product divided by that of pure water at the same temperature; therefore, pure distilled water has a water activity of exactly one.

The compositions of the present invention may be cleansing, protective, treatment or care creams, skincare lotions, gels or foams, such as cleansing or disinfecting lotions, bath compositions or deodorant compositions.

As regards more particularly the compositions for external topical administration, they may be aqueous, aqueous-alcoholic or oily solutions, solutions or dispersions of the lotion or serum type, emulsions of liquid or semi-liquid consistency, of the milk type, obtained by dispersion of a fatty phase in an aqueous phase (O/W) or vice-versa (W/O), or suspensions or emulsions of soft, semi-solid or solid consistency, of the cream type, aqueous or anhydrous gels, microemulsions, microcapsules, microparticles, or vesicular dispersions of ionic and/or non-ionic type.

A topical composition according to the invention may advantageously be formulated in any galenical form that is suitable for haircare, especially in the form of a hair lotion, a shampoo, especially an antidandruff shampoo, a hair conditioner, a detangler, a hair cream or gel, a styling lacquer, a hairsetting lotion, a treating lotion, a dye composition (especially for oxidation dyeing) optionally in the form of a colouring shampoo, a hair-restructuring lotion, a permanent-waving composition, a lotion or gel for combating hair loss, an antiparasitic shampoo or a medicated shampoo, especially an anti-seborrhoea shampoo, a scalp care product, which is especially anti-irritant, anti-ageing or restructuring, or which activates the blood circulation.

When the composition of the invention is an emulsion, the proportion of the fatty phase may range from 5% to 80% by weight, and preferably from 10% to 50% by weight, relative to the total weight of the composition. The oils, the emulsifiers and the coemulsifiers used in the composition in emulsion form are chosen from those conventionally used in the cosmetics and/or dermatological field. The emulsifier and the coemulsifier may be present, in the composition, in a proportion ranging from 0.3% to 30% by weight, and preferably from 0.5% to 20% by weight, relative to the total weight of the composition.

When the composition of the invention is an oily gel or solution, the fatty phase may represent more than 90% of the total weight of the composition.

The galenic forms for topical administration may also contain adjuvants that are customary in the cosmetics, pharmaceutical and/or dermatological field, such as hydrophilic or lipophilic gelling agents, hydrophilic or lipophilic active agents, preservatives, antioxidants, solvents, fragrances, fillers, screens, odour absorbers and dyestuffs. The amounts of these various adjuvants are those conventionally used in the field under consideration, and are, for example, from 0.01% to 20% of the total weight of the composition. Depending on their nature, these adjuvants may be introduced into the fatty phase and/or into the aqueous phase.

As fatty substances that may be used in the invention, mention may be made of mineral oils such as, for example, hydrogenated polyisobutene and liquid petroleum jelly, plant oils such as, for example, a liquid fraction of shea butter, sunflower oil and apricot kernel oil, animal oils such as, for example, perhydrosqualene, synthetic oils, in particular Purcellin oil, isopropyl myristate and ethylhexyl palmitate, unsaturated fatty acids and fluoro oils such as, for example, perfluoropolyethers. Use may also be made of fatty alcohols, fatty acids such as, for example, stearic acid and such as, for example, waxes, in particular paraffin wax, carnauba wax and beeswax. Use may also be made of silicone compounds such as silicone oils and, for example, cyclomethicone and dimethicone, and silicone waxes, resins and gums.

As emulsifiers that may be used in the invention, mention may, for example, be made of glyceryl stearate, polysorbate 60, the mixture of cetylstearyl alcohol/oxyethylenated cetylstearyl alcohol comprising 33 mol of ethylene oxide, sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyl dimethicone copolyol and sorbitan monostearate or tristearate, PEG-40 stearate, or oxyethylenated sorbitan monostearate (20 EO).

As solvents that may be used in the invention, mention may be made of lower alcohols, especially ethanol and isopropanol, and propylene glycol.

The composition of the invention may also advantageously contain a spring and/or mineral water, in particular chosen from Vittel water, waters from the Vichy basin, and la Roche Posay water.

As hydrophilic gelling agents, mention may be made of carboxylic polymers such as carbomer, acrylic copolymers such as acrylate/alkyl acrylate copolymers, polyacrylamides, and in particular the mixture of polyacrylamide, C13-14 isoparaffin and Laureth-7 sold under the name Sepigel 305° by the company SEPPIC, polysaccharides, for instance derivatives such as hydroxyalkylcelluloses, and in particular hydroxypropylcellulose and hydroxyethylcellulose, natural gums such as guar gum, locust bean gum, carob and xanthan gum, and clays.

As lipophilic gelling agents, mention may be made of modified clays such as bentones, metal salts of fatty acids, such as aluminium stearates and hydrophobic silica, or else ethylcellulose and polyethylene.

The compositions according to the invention may also be solid preparations constituting cleansing soaps or bars.

They may also be used for the scalp in the form of solutions, creams, gels, emulsions or mousses, or alternatively in the form of aerosol compositions also containing a propellant under pressure.

In the case of oral use in accordance with the invention for oral administration, the use of an ingestible support or carrier is preferred. The ingestible support or carrier may be of diverse nature depending on the type of composition under consideration.

Milk, yogurt, cheese, fermented milks, milk-based fermented products, ice creams, cereal-based products or fermented cereal-based products, breakfast cereals, cereal or granola bars, milk-based powders, infant and baby formulas, food products of confectionery, chocolate or cereal type, animal feed, in particular for domestic animals, tablets, gel capsules or lozenges, liquid bacterial suspensions, oral supplements in dry form and oral supplements in liquid form are especially suitable for use as ingestible support or carrier.

The composition according to the invention to be administered orally may be formulated for example in the form of coated tablets, gel capsules, gels, emulsions, tablets, capsules, hydrogels, food bars, compact or loose powders, liquid suspensions or solutions, confectionery products, fermented milks, fermented cheeses, chewing gum, toothpaste or spray solutions or food carriers.

Tablets or lozenges, oral supplements in dry form and oral supplements in liquid form are suitable for use as dietetic or pharmaceutical supports or food carriers.

The composition may be, for example, a food supplement, which may be formulated via the usual processes for in particular producing sugar-coated tablets, gel capsules, gels, emulsions, tablets, capsules and hydrogels allowing controlled release.

In particular, a microorganism according to the invention may be incorporated into all forms of food supplements or enriched foods, for example food bars or compacted or non-compacted powders. The powders may be diluted in water, soda, milk products or soya bean derivatives, or may be incorporated into food bars.

A microorganism of the invention, a fraction thereof and/or a metabolite thereof, may moreover be formulated with the usual excipients and components for such oral compositions or food supplements, i.e. in particular fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein.

In therapeutic applications, compositions are administered in an amount sufficient to at least partially cure or arrest the symptoms of a disease and its complications. An amount adequate to accomplish this is defined as "a therapeutically effective dose". Amounts effective for this purpose will depend on a number of factors known to those of skill in the art such as the severity of the disease and the weight and general state of the patient.

In prophylactic applications, compositions according to the invention are administered to a patient susceptible to or otherwise at risk of a particular disease in an amount that is sufficient to at least partially reduce the risk of developing a disease. Such an amount is defined to be "a prophylactically effective dose". Again, the precise amounts depend on a number of patient specific factors such as the patient's state of health and weight.

The compositions of the present invention comprise at least one natural derivative of the *Lactobacillus johnsonii* strain CNCM I-1225 and/or the cell-free culture supernatant of the present invention in a therapeutically or prophylactically effective dose.

Those skilled in the art will be able to adjust dosage accordingly.

For example, the composition may comprise the natural derivative of the *Lactobacillus johnsonii* strain CNCM I-1225 in accordance with the present invention in an amount of $10^6$-$10^{12}$ cfu, for example $10^8$ to $10^{10}$ cfu per daily dose.

Previous work has also shown that non-replicating *L. johnsonii* CNCM I-1225 may be used in the treatment or prevention of disorders related to the immune system including infections, see WO 2010/133475, fully incorporated herein by reference. It was found that *L. johnsonii* CNCM I-1225 strongly induces the constitutive hBD1 expression, and that heat-treated *L. johnsonii* CNCM I-1225 up-regulates hBD1 more strongly than its live counterpart.

Consequently, the natural derivative of the *Lactobacillus johnsonii* strain CNCM I-1225 in accordance with the present invention may also be present in a non-replicating form.

"Non-replicating" natural derivatives of the *Lactobacillus johnsonii* strain CNCM I-1225 include derivatives, which have been heat treated. This includes natural derivatives of the *Lactobacillus johnsonii* strain CNCM I-1225 that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

Obviously, non-replicating micro-organisms do not form colonies, consequently, this term is to be understood as the amount of non replicating micro-organisms that is obtained from $10^6$ and $10^{12}$ cfu/g replicating bacteria.

The composition may also comprise the natural derivative of the *Lactobacillus johnsonii* strain CNCM I-1225 in accordance with the present invention in an amount of 0.005 mg-5000 mg, for example 0.5 mg to 50 mg, per daily dose.

Those skilled in the art will understand that they can freely combine all features of the present invention described herein, without departing from the scope of the invention as disclosed. In particular, features described for the uses of the present invention may be applied to the foodstuff of the present invention and vice versa.

Further advantages and features of the present invention are apparent from the following Examples and Figures.

FIG. 3 shows the gene sequence of the *Lactobacillus johnsonii* CNCM I-1225 D-lactate dehydrogenase gene (SEQ ID NO: 1) and the changes identified in the corresponding gene in *Lactobacillus johnsonii* CNCM I-4437 being circled. The translated D-lactate dehydrogenase enzyme (SEQ ID NO: 2) is also shown with the corresponding changes for *Lactobacillus johnsonii* CNCM I-4437.

FIG. 4A shows the gene sequence of the *Lactobacillus johnsonii* CNCM I-4437 D-lactate dehydrogenase gene (SEQ ID NO: 6) with the base at position 230 boxed and altered compared to the parent strain *Lactobacillus johnsonii* CNCM I-1225 (G).

FIG. 4B shows the protein sequence of the *Lactobacillus johnsonii* CNCM I-4437 D-lactate dehydrogenase enzyme (SEQ ID NO: 7) with the amino acid at position 77 boxed and altered compared to the parent strain *Lactobacillus johnsonii* CNCM I-1225 (R).

EXAMPLE 1

Figure 1:
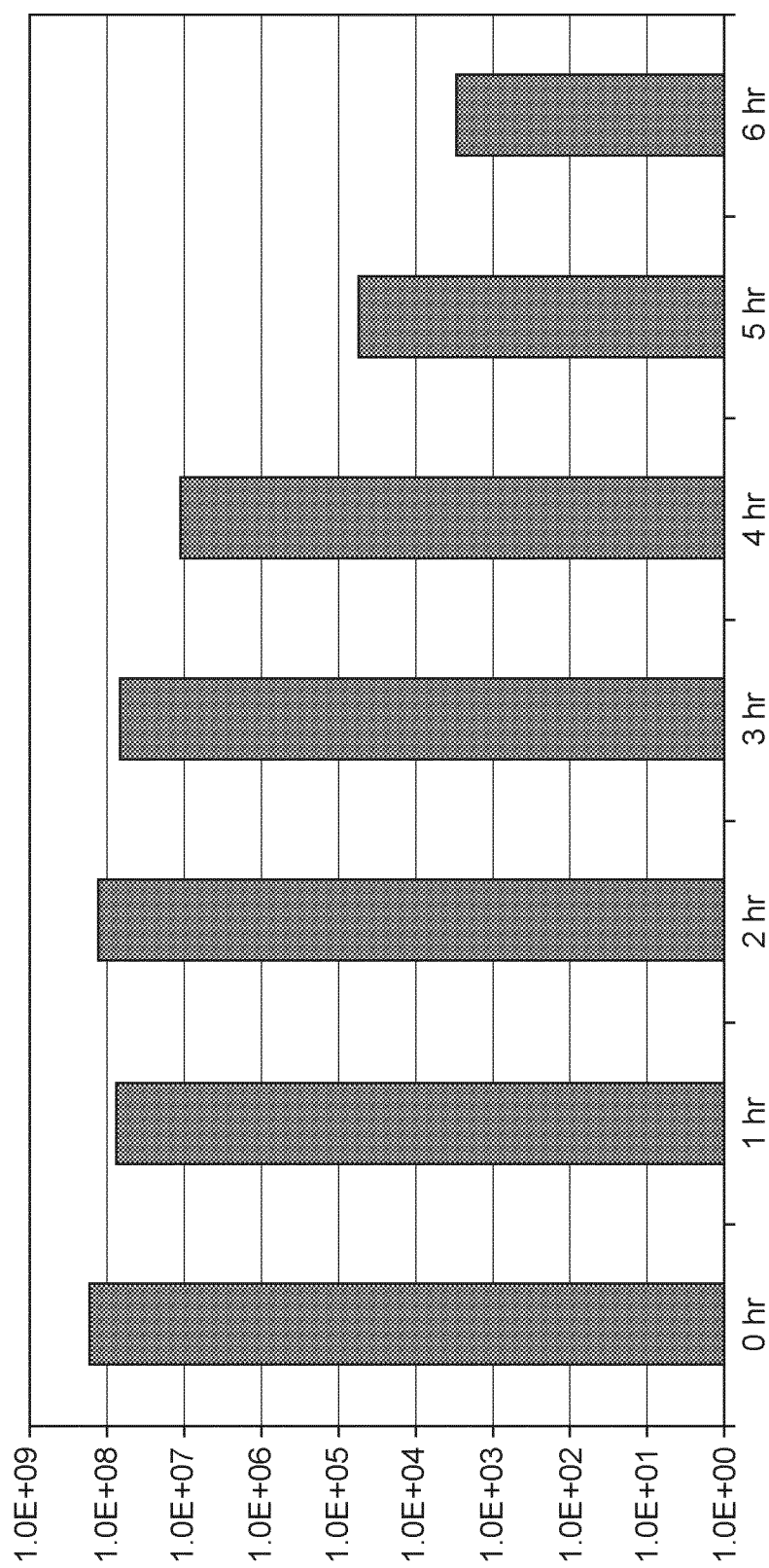
FIG. 1 shows the 'survival curve' for *Lactobacillus johnsonii* CNCM I-1225 treated with ethyl methane sulfonate.

Ethyl methane sulfonate treatment of *Lactobacillus johnsonii* CNCM I-1225 cultures. Samples of 1001 containing approximately $10^8$ colony forming units of a 16 hr *Lactobacillus johnsonii* CNCM I-1225 culture were washed 3 times with Dulbecco's phosphate buffered saline. The cells were finally suspended in 1 ml PBS and 0 or 10 µl ethyl methane sulfonate added and incubated at 37° C. without shaking. The treated cells were washed twice in PBS, the CFU of treated and not treated cultures determined and plotted as survivors to give the 'survival curve' shown in FIG. 1. The conditions producing 1% survivors were initially targeted and bracketed with time points before and after, the cells diluted and plated as single colonies on MRS plates for enumeration. The remaining treated cells were then used to inoculate 10 ml of MRS broth and incubated for 16 hr growth at 37° C. The culture was then diluted and spread on MRS plates to produce individual colonies for screening.

Figure 2:
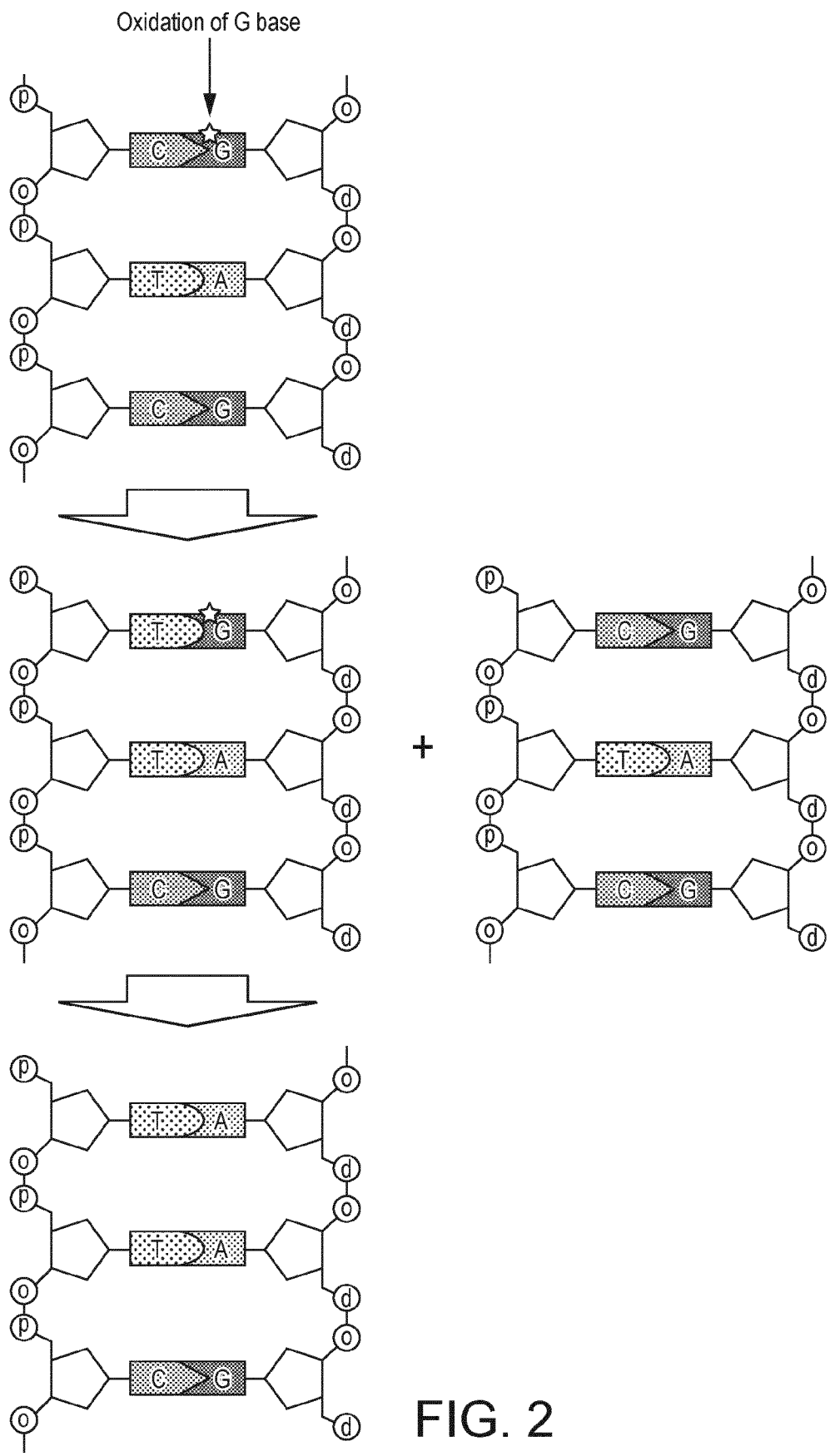
FIG. 2 shows the molecular process of natural mutations from the oxidation of a G base to the segregation of the DNA strands resulting in a mixture of parent and modified DNA types and a mixed parent and modified colony.

Mutations occur naturally in bacteria mainly through the oxidation of guanosine (G) residues in double stranded DNA and typically produces single base-pair changes when resolved by DNA replication as shown in FIG. 2. This results in a natural mutation profile of G to adenosine (A) and cytidine (C) to thymidine (T) changes, depending on which DNA strand is sequenced. Ethyl methane sulfonate acts by chemical oxidation of G bases and results in the same mutation profile as natural mutations, namely G to A and C to T, depending on which DNA strand is sequenced. This was confirmed later by DNA sequencing of the D-lactate dehydrogenase genes and genome sequences where the vast majority of the observed changes were either G to A or C to T.

EXAMPLE 2

Screening of individual colonies for strains deficient in D-lactic acid production. Individual ethyl methane sulfonate treated colonies were picked into 96-well plates containing 200 µl MRS broth and incubated at 37° C. for 24 hr to form mini cultures. The growth of the cultures was estimated by absorbance at 620 nm using a Tecan sunrise microplate reader. Ten µl of the culture supernatant was mixed with 190 µl of a reaction mixture containing 100 mM Tris HCl pH 9, 2.5 mM EDTA pH 8.0, 20 U/ml D-lactate dehydrogenase (from *Leuconostoc mesenteroides*), 1 mg/ml NAD (β-nicotinamide adenine dinucleotide) plus 3% hydrazinium hydroxide and incubated at room temperature for 1 hr. The absorbance at 320 nm (formation of β-NADH) was then measured using the Tecan sunrise microplate reader and the data exported to excel for analysis. On each plate controls containing MRS alone and *Lactobacillus johnsonii* CNCM I-1225 culture supernatant at 5%, 25%, 50% or 100% concentrations were included as standards for normalisation of the data.

This is a phenotypic analysis of the isolated colonies to determine the presence or absence of D-lactic acid in the culture medium after growth. When screening individual colonies for the presence of D-lactic acid it is also clear that 'mixed' cultures containing 50% of a D-lactic acid producer and 50% of a D-lactic acid non-producer will result in a culture that is 'positive' for the presence of D-lactic acid. The D-lactic acid deficient phenotype that we target is therefore considered as 'recessive' to the D-lactic acid production phenotype. This is important when we consider the schematic of mutagenesis shown in FIG. 2 as a single oxidised G base will result in a final colony that is a mixture of both parent and altered individuals and hence phenotypically, D-lactic acid positive. In this case the inclusion of the growth in MRS broth after ethyl methane sulfonate treatment was essential for the isolation of strains deficient in D-lactic acid production. After screening some 21,000 individual ethyl methane sulfonate treated colonies, 15 colonies deficient in D-lactic acid production were isolated and subjected to further analysis.

EXAMPLE 3

Determination of D-lactic acid levels in culture medium. Cultures were grown in MRS broth at 37° C. for 16 hours and the bacteria removed by centrifugation. To determine D-lactic acid concentrations, the cell-free culture supernatants were diluted in water, analysed as described above and compared to a standard curve prepared with dilutions of sodium D-lactic acid. L-lactic acid concentrations were determined in the same way by exchanging the enzyme D-lactate dehydrogenase with rabbit muscle L-lactic dehydrogenase and using sodium L-lactic acid as standard. The results of this analysis for CNCM I-4437 are shown in Table 1 and include the controls of *Lactobacillus johnsonii* CNCM I-1225, *Lactobacillus johnsonii* NCC9006 with a GMO inactivated D-lactate dehydrogenase gene and *Lactobacillus paracasei* NCC2461 and *Lactobacillus rhamnosus* NCC4007, both considered as L-lactic acid producing strains.

*Lactobacillus paracasei* NCC2461 (accession number: CNCM I-2116) was deposited under the Budapest Treaty on 12 Jan. 1999, with the CNCM (address already mentioned). *Lactobacillus rhamnosus* NCC4007 (accession number: CGMCC 1.3724) was deposited under the Budapest Treaty in October 2004, with the China General Microbiological Culture Collection Center (CGMCC), Institute of Microbiology, Chinese Academy of Sciences, No. 1, West Beichen Road, Chaoyang District, Beijing 100101, China. *Lactobacillus johnsonii* NCC9006 is the strain deriving from *Lactobacillus johnsonii* La1, as described in the article by Lapierre et al. entitled "D-Lactate Dehydrogenase Gene (IdhD) Inactivation and Resulting Metabolic Effects in the *Lactobacillus johnsonii* Strains La1 and N312" (Appl. Environ. Microbiol. 1999, 65(9):4002).

TABLE 1

Values of D- and L-lactic acid determined for CNCM I-1225, CNCM I-4437 from cell-free cultures. Included as controls are the strains NCC9006, a *Lactobacillus johnsonii* strain with a GMO inactivation of the D-lactate dehydrogenase gene, *Lactobacillus paracasei* NCC2461 and *Lactobacillus rhamnosus* NCC4007, both considered as L-lactic acid producing strains. Experiments were performed in triplicate and are given as the mean value plus standard deviation in brackets.

| Strain | Total lactic acid * | L-lactic acid | D-lactic acid | % D-lactic acid |
|---|---|---|---|---|
| CNCM I-1225 | 14 | 4.8 (0.17) | 9.2 (0.27) | 65.7 |
| CNCM I-4437 | 21.2 | 21.1 (0.53) | 0.14 ** | 0.7 |
| NCC9006 | 21.2 | 21.2 (3.25) | <0.05 *** | <0.3 **** |
| NCC2461 | 16.8 | 16.3 (0.97) | 0.48 (0.02) | 2.9 |
| NCC4007 | 15.8 | 15.2 (0.49) | 0.56 (0.03) | 3.5 |

* lactic acid values in g/l.
** only one of the samples gave a value above the lower quantification limit.
*** below the lower quantification limit.
**** % calculated using the lower quantification limit value.

The results show that the D-lactic acid production values for *Lactobacillus johnsonii* CNCM I-1225 are approximately 65% of total lactic acid and that the D-lactic acid production values for *Lactobacillus johnsonii* CNCM I-4437 are greatly reduced. The D-lactic acid production levels for *Lactobacillus johnsonii* CNCM I-4437 are very low and below 1% of total lactic acid. This result is similar to the results obtained for the *Lactobacillus johnsonii* NCC9006 containing an inactivated D-lactate dehydrogenase gene created using gene technology methods. Also of note are the control strains *Lactobacillus paracasei* NCC2461 and *Lactobacillus rhamnosus* NCC4007, both considered as L-lactic acid producers, and which produce 3 and 3.5% D-lactic acid under these conditions, respectively. From these data the strain *Lactobacillus johnsonii* CNCM I-4437 can be considered as a L-lactic acid producer and phenotypically distinct from *Lactobacillus johnsonii* CNCM I-1225.

EXAMPLE 4

Figure 3:
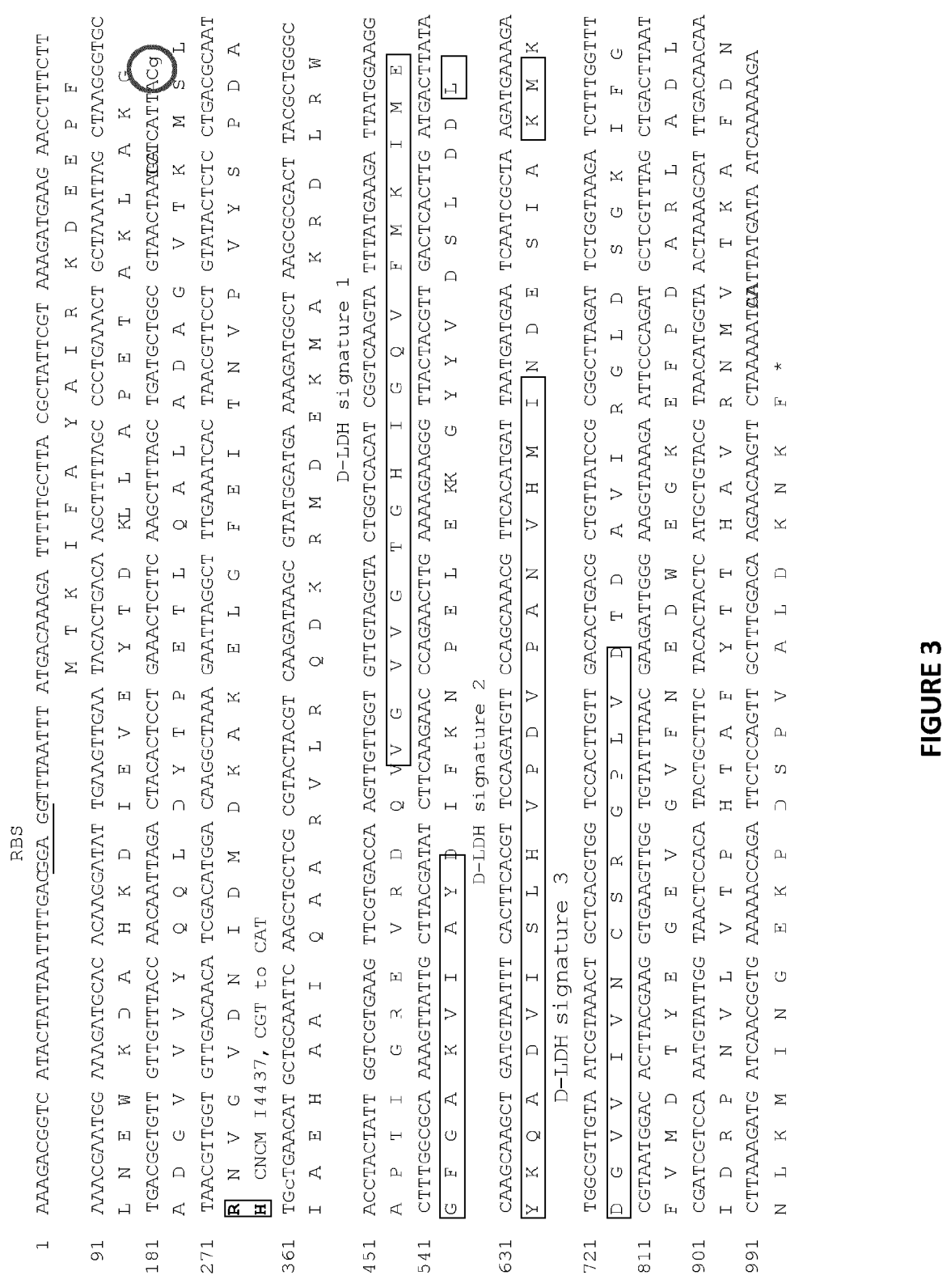

Identification of changes in the D-lactate dehydrogenase genes. In order to identify the changes in the D-lactate dehydrogenase gene responsible for the D-lactic acid deficient phenotype, we PCR amplified the regions for DNA sequence analysis. The region was amplified from one µl of bacterial culture using the primers P1 TCAGCACATAACCAGCAGCT (SEQ ID NO: 3) plus P2 GCAATAATACTGTCGCCGGT (SEQ ID NO: 4). The amplicons were purified and sequenced with primers P1, P3 GTGTATAATAAAAGACGGTC (SEQ ID NO: 5) plus P2, compiled and analysed in the DNASTAR suite of programs. The results are shown in FIG. 3. As can be seen in FIG. 3, the strain *Lactobacillus johnsonii* CNCM I-4437 contains a G to A change at base pair 270 of FIG. 3 and FIG. 4A, and which results in a arginine to histidine amino acid change at position 77 (R77H) positioned outside the conserved signature domains of the D-lactate dehydrogenase enzyme sequence (FIG. 4B). The gene sequencing data shows that the D-lactic acid deficient production phenotype in *Lactobacillus johnsonii* CNCM I-4437 is accompanied by a corresponding change in the D-lactate dehydrogenase gene and enzyme sequence.

EXAMPLE 5

Determination of the phenotypic stability of *Lactobacillus johnsonii* CNCM I-4437. Given the large number of generations from the culture collection to the final product, it is important that the D-lactic acid deficient phenotype is stable and that reversion to production of D-lactic acid is very rare. To investigate this we cultivated *Lactobacillus johnsonii* CNCM I-4437 in MRS broth for a total of 100 generations and then tested 300 individual colonies for D-lactic acid production. The results are that none of the colonies tested showed D-lactic acid levels above that determined for strain *Lactobacillus johnsonii* CNCM I-4437. This analysis was also performed after pilot-scale production of spray-dried powders and Lc1 Drink products with the same results.

In lactic acid bacteria a single copy of D- or L-lactate dehydrogenase is essential for the production of lactic acid and the regeneration of NADH, a co-factor in this reaction, to NAD. In lactic acid bacteria this is the only route to regenerate NAD under anaerobic conditions and is essential for growth. In the case of the D-lactic acid deficient strains there is no selective pressure for the reversion to D-lactic acid production as the L-lactate dehydrogenase enzyme is sufficient to cover the lack of D-lactate dehydrogenase enzyme activity.

EXAMPLE 6

Survival of *Lactobacillus johnsonii* CNCM I-1225 and *Lactobacillus johnsonii* CNCM I-4437 in Lc1 Drink products. Survival of probiotic bacteria during product storage is an important factor to ensure the expected $10^7$ colony forming units after 45 days storage. The reason for loss of viability is not fully understood but there appears to be some evidence for the involvement of oxygen. To test whether *Lactobacillus johnsonii* CNCM I-4437 survives at least as well as *Lactobacillus johnsonii* CNCM I-1225 under simulated storage conditions, we took fresh Lc1 Drink products and eliminated the living bacteria by heating to 85° C. for 10 minutes. Then either *Lactobacillus johnsonii* CNCM I-1225 or *Lactobacillus johnsonii* CNCM I-4437 were inoculated into the sterile products, the bottles sealed and stored under standard test conditions at either 8° C. or 15° C. for 45 days. The results from three independent trials are shown below. To our surprise *Lactobacillus johnsonii* CNCM I-4437 shows a consistently better survival than *Lactobacillus johnsonii* CNCM I-1225 at both temperatures and in all three trials with improvements ranging from 0.42 logs to over 2 logs.

| Trial 1. | | | | |
|---|---|---|---|---|
| Storage temp | Strain | T = 0 | T = 45 days | Log loss |
| 8° C. | CNCM I-1225 | 8.08 | 7.2 | −0.88 |
| | CNCM I-4437 | 8.04 | 7.62 | −0.42 |
| 15° C. | CNCM I-1225 | 8.08 | 6.36 | −1.72 |
| | CNCM I-4437 | 8.04 | 7.18 | −0.87 |

| Trial 2. | | | | |
|---|---|---|---|---|
| Storage temp | Strain | T = 0 | T = 45 days | Log loss |
| 8° C. | CNCM I-1225 | 7.93 | 6.46 | −1.47 |
| | CNCM I-4437 | 7.79 | 6.84 | −0.95 |
| 15° C. | CNCM I-1225 | 7.93 | 5.6 | −2.33 |
| | CNCM I-4437 | 7.79 | 6.7 | −1.09 |

Trial 3.

| Storage temp | Strain | T = 0 | T = 45 days | Log loss |
|---|---|---|---|---|
| 8° C. | CNCM I-1225 | 8.23 | 6.2 | −2.03 |
| | CNCM I-4437 | 7.91 | 7.41 | −0.49 |
| 15° C. | CNCM I-1225 | 8.23 | 5.85 | −2.38 |
| | CNCM I-4437 | 7.91 | 6.83 | −1.08 |

Listing of SEQ IDs:

| SEQ ID NO: (DNA) | SEQ ID NO: (protein) | Short description |
|---|---|---|
| 1 | 2 | *Lactobacillus johnsonii* CNCM I-1225 D-lactate dehydrogenase |
| 3 | n/a | Primer P1 (see example 4) |
| 4 | n/a | Primer P2 (see example 4) |
| 5 | n/a | Primer P3 (see example 4) |
| 6 | 7 | *Lactobacillus johnsonii* CNCM I-4437 D-lactate dehydrogenase (FIGS. 4A and 4B) |

The invention claimed is:

1. A method for the treatment or prevention of disorders linked to a weakened immune system comprising administering to an individual in need of same a composition comprising *Lactobacillus johnsonii* strain CNCM I-4437.

2. The method as claimed in claim 1, wherein the disorder linked to a weakened immune system is selected from the group consisting of flu, rhinitis, common cold, and combinations thereof.

3. The method as claimed in claim 2, wherein the composition is selected from the group consisting of food compositions, petfood compositions, drinks, dairy products, nutritional formulas, food additives, nutraceuticals, pharmaceutical compositions, food ingredients and cosmetic compositions.

4. The method as claimed in claim 2, wherein the composition is selected from the group consisting of acidified milk products and milk based powders.

5. The method as claimed in 2, wherein the composition comprises the *Lactobacillus johnsonii* strain CNCM I-4437 in an amount of $10^6$-$10^{12}$ cfu per daily dose.

6. The method as claimed in claim 1, wherein the composition is selected from the group consisting of food compositions, petfood compositions, drinks, dairy products, nutritional formulas, food additives, nutraceuticals, pharmaceutical compositions, food ingredients and cosmetic compositions.

7. The method as claimed in claim 1, wherein the composition is selected from the group consisting of acidified milk products and milk based powders.

8. The method as claimed in claim 1, wherein the composition comprises the *Lactobacillus johnsonii* strain CNCM I-4437 in an amount of $10^6$-$10^{12}$ cfu per daily dose.

* * * * *

SEQUENCE LISTING

<160> NUMBER OF SEQ ID NOS: 7

<210> SEQ ID NO 1
<211> LENGTH: 1080
<212> TYPE: DNA
<213> ORGANISM: Lactobacillus johnsonii

<400> SEQUENCE: 1

```
aaagacggtc atactattaa ttttgacgga ggtttaattt atgacaaaga tttttgctta      60
cgctattcgt aaagatgaag aacctttctt aaacgaatgg aaagatgcac acaaggatat     120
tgaagttgaa tacactgaca agcttttagc ccctgaaact gctaaattag ctaagggtgc     180
tgacggtgtt gttgtttacc aacaattaga ctacactcct gaaactcttc aagctttagc     240
tgatgctggc gtaactaaga tgtcattacg taacgttggt gttgacaaca tcgacatgga     300
caaggctaaa gaattaggct ttgaaatcac taacgttcct gtatactctc ctgacgcaat     360
tgctgaacat gctgcaattc aagctgctcg cgtactacgt caagataagc gtatggatga     420
aaagatggct aagcgcgact acgctgggc acctactatt ggtcgtgaag ttcgtgacca     480
agttgttggt gttgtaggta ctggtcacat cggtcaagta tttatgaaga ttatggaagg     540
ctttggcgca aaagttattg cttacgatat cttcaagaac ccagaacttg aaaagaaggg     600
ttactacgtt gactcacttg atgacttata caagcaagct gatgtaattt cacttcacgt     660
tccagatgtt ccagcaaacg ttcacatgat taatgatgaa tcaatcgcta agatgaaaga     720
tggcgttgta atcgtaaact gctcacgtgg tccacttgtt gacactgacg ctgttatccg     780
cggcttagat tctggtaaga tctttggttt cgtaatggac acttacgaag gtgaagttga     840
tgtatttaac gaagattggg aaggtaaaga attcccagat gctcgtttag ctgacttaat     900
cgatcgtcca aatgtattgg taactccaca tactgctttc tacactactc atgctgtacg     960
taacatggta actaaagcat ttgacaacaa cttaaagatg atcaacggtg aaaaaccaga    1020
ttctccagtt gctttggaca agaacaagtt ctaaaaatca aattatgata atcaaaaaga    1080
```

<210> SEQ ID NO 2
<211> LENGTH: 337
<212> TYPE: PRT
<213> ORGANISM: Lactobacillus johnsonii

<400> SEQUENCE: 2

Met Thr Lys Ile Phe Ala Tyr Ala Ile Arg Lys Asp Glu Glu Pro Phe
1               5                   10                  15

Leu Asn Glu Trp Lys Asp Ala His Lys Asp Ile Glu Val Glu Tyr Thr
            20                  25                  30

Asp Lys Leu Leu Ala Pro Glu Thr Ala Lys Leu Ala Lys Gly Ala Asp
        35                  40                  45

```
Gly Val Val Tyr Gln Gln Leu Asp Tyr Thr Pro Glu Thr Leu Gln
 50              55                  60

Ala Leu Ala Asp Ala Gly Val Thr Lys Met Ser Leu Arg Asn Val Gly
 65                  70                  75                  80

Val Asp Asn Ile Asp Met Asp Lys Ala Lys Glu Leu Gly Phe Glu Ile
                 85                  90                  95

Thr Asn Val Pro Val Tyr Ser Pro Asp Ala Ile Ala Glu His Ala Ala
             100                 105                 110

Ile Gln Ala Ala Arg Val Leu Arg Gln Asp Lys Arg Met Asp Glu Lys
         115                 120                 125

Met Ala Lys Arg Asp Leu Arg Trp Ala Pro Thr Ile Gly Arg Glu Val
130                 135                 140

Arg Asp Gln Val Val Gly Val Gly Thr Gly His Ile Gly Gln Val
145                 150                 155                 160

Phe Met Lys Ile Met Glu Gly Phe Gly Ala Lys Val Ile Ala Tyr Asp
                165                 170                 175

Ile Phe Lys Asn Pro Glu Leu Glu Lys Lys Gly Tyr Tyr Val Asp Ser
             180                 185                 190

Leu Asp Asp Leu Tyr Lys Gln Ala Asp Val Ile Ser Leu His Val Pro
         195                 200                 205

Asp Val Pro Ala Asn Val His Met Ile Asn Asp Glu Ser Ile Ala Lys
210                 215                 220

Met Lys Asp Gly Val Val Ile Val Asn Cys Ser Arg Gly Pro Leu Val
225                 230                 235                 240

Asp Thr Asp Ala Val Ile Arg Gly Leu Asp Ser Gly Lys Ile Phe Gly
                245                 250                 255

Phe Val Met Asp Thr Tyr Glu Gly Glu Val Gly Val Phe Asn Glu Asp
             260                 265                 270

Trp Glu Gly Lys Glu Phe Pro Asp Ala Arg Leu Ala Asp Leu Ile Asp
         275                 280                 285

Arg Pro Asn Val Leu Val Thr Pro His Thr Ala Phe Tyr Thr Thr His
290                 295                 300

Ala Val Arg Asn Met Val Thr Lys Ala Phe Asp Asn Asn Leu Lys Met
305                 310                 315                 320

Ile Asn Gly Glu Lys Pro Asp Ser Pro Val Ala Leu Asp Lys Asn Lys
                325                 330                 335

Phe

<210> SEQ ID NO 3
<211> LENGTH: 20
<212> TYPE: DNA
<213> ORGANISM: Lactobacillus johnsonii

<400> SEQUENCE: 3
tcagcacata accagcagct                                            20

<210> SEQ ID NO 4
<211> LENGTH: 20
<212> TYPE: DNA
<213> ORGANISM: Lactobacillus johnsonii

<400> SEQUENCE: 4
gcaataatac tgtcgccggt                                            20

<210> SEQ ID NO 5
```

```
<211> LENGTH: 20
<212> TYPE: DNA
<213> ORGANISM: Lactobacillus johnsonii

<400> SEQUENCE: 5
gtgtataata aaagacggtc                                                   20

<210> SEQ ID NO 6
<211> LENGTH: 1014
<212> TYPE: DNA
<213> ORGANISM: Lactobacillus johnsonii

<400> SEQUENCE: 6
atgacaaaga tttttgctta cgctattcgt aaagatgaag aacctttctt aaacgaatgg       60
aaagatgcac acaaggatat tgaagttgaa tacactgaca gcttttagc ccctgaaact      120 gctaaattag ctaagggtgc tgacggtgtt gttgtttacc aacaattaga ctacactcct      180
gaaactcttc aagctttagc tgatgctggc gtaactaaga tgtcattaca taacgttggt      240
gttgacaaca tcgacatgga caaggctaaa gaattaggct tgaaatcac taacgttcct      300 gtatactctc ctgacgcaat tgctgaacat gctgcaattc aagctgctcg cgtactacgt      360
caagataagc gtatggatga aaagatggct aagcgcgact acgctgggc acctactatt      420 ggtcgtgaag ttcgtgacca agttgttggt gttgtaggta ctggtcacat cggtcaagta      480
tttatgaaga ttatggaagg cttttggcgca aaagttattg cttacgatat cttcaagaac      540
ccagaacttg aaaagaaggg ttactacgtt gactcacttg atgacttata caagcaagct      600
gatgtaattt cacttcacgt tccagatgtt ccagcaaacg ttcacatgat taatgatgaa      660
tcaatcgcta agatgaaaga tggcgttgta atcgtaaact gctcacgtgg tccacttgtt      720
gacactgacg ctgttatccg cggcttagat tctggtaaga tctttggttt cgtaatggac      780
acttacgaag gtgaagttgg tgtatttaac gaagattggg aaggtaaaga attcccagat      840
gctcgtttag ctgacttaat cgatcgtcca aatgtattgg taactccaca tactgctttc      900
tacactactc atgctgtacg taacatggta actaaagcat ttgacaacaa cttaaagatg      960
atcaacggtg aaaaaccaga ttctccagtt gctttggaca agaacaagtt ctaa            1014

<210> SEQ ID NO 7
<211> LENGTH: 337
<212> TYPE: PRT
<213> ORGANISM: Lactobacillus johnsonii

<400> SEQUENCE: 7

Met Thr Lys Ile Phe Ala Tyr Ala Ile Arg Lys Asp Glu Glu Pro Phe
1               5                   10                  15

Leu Asn Glu Trp Lys Asp Ala His Lys Asp Ile Glu Val Glu Tyr Thr
            20                  25                  30

Asp Lys Leu Leu Ala Pro Glu Thr Ala Lys Leu Ala Lys Gly Ala Asp
        35                  40                  45

Gly Val Val Val Tyr Gln Gln Leu Asp Tyr Thr Pro Glu Thr Leu Gln
    50                  55                  60

Ala Leu Ala Asp Ala Gly Val Thr Lys Met Ser Leu His Asn Val Gly
65                  70                  75                  80

Val Asp Asn Ile Asp Met Asp Lys Ala Lys Glu Leu Gly Phe Glu Ile
                85                  90                  95

Thr Asn Val Pro Val Tyr Ser Pro Asp Ala Ile Ala Glu His Ala Ala
            100                 105                 110
```

```
Ile Gln Ala Ala Arg Val Leu Arg Gln Asp Lys Arg Met Asp Glu Lys
            115                 120                 125

Met Ala Lys Arg Asp Leu Arg Trp Ala Pro Thr Ile Gly Arg Glu Val
    130                 135                 140

Arg Asp Gln Val Val Gly Val Val Gly Thr Gly His Ile Gly Gln Val
145                 150                 155                 160

Phe Met Lys Ile Met Glu Gly Phe Gly Ala Lys Val Ile Ala Tyr Asp
                165                 170                 175

Ile Phe Lys Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Glu Ser Ile Ala Lys
        210                 215                 220

Met Lys Asp Gly Val Val Ile Val Asn Cys Ser Arg Gly Pro Leu Val
225                 230                 235                 240

Asp Thr Asp Ala Val Ile Arg Gly Leu Asp Ser Gly Lys Ile Phe Gly
                245                 250                 255

Phe Val Met Asp Thr Tyr Glu Gly Glu Val Gly Val Phe Asn Glu Asp
                260                 265                 270

Trp Glu Gly Lys Glu Phe Pro Asp Ala Arg Leu Ala Asp Leu Ile Asp
            275                 280                 285

Arg Pro Asn Val Leu Val Thr Pro His Thr Ala Phe Tyr Thr Thr His
        290                 295                 300

Ala Val Arg Asn Met Val Thr Lys Ala Phe Asp Asn Asn Leu Lys Met
305                 310                 315                 320

Ile Asn Gly Glu Lys Pro Asp Ser Pro Val Ala Leu Asp Lys Asn Lys
                325                 330                 335

Phe
```